US008354520B2

(12) United States Patent
Juo et al.

(10) Patent No.: US 8,354,520 B2
(45) Date of Patent: Jan. 15, 2013

(54) COMPOSITION AND METHOD FOR TREATING ATHEROSCLEROSIS, METHOD FOR DETERMINING IF A SUBJECT HAS ATHEROSCLEROSIS AND METHOD OF SCREENING AN ANTI-ATHEROSCLEROTIC DRUG

(75) Inventors: Suh-Hang Hank Juo, Kaohsiung (TW); Yung-Song Wang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 324 days.

(21) Appl. No.: 12/635,178

(22) Filed: Dec. 10, 2009

(65) Prior Publication Data

US 2011/0142913 A1    Jun. 16, 2011

(51) Int. Cl.
*C07H 21/04*    (2006.01)
(52) U.S. Cl. ..................................... 536/24.5
(58) Field of Classification Search .................. None
See application file for complete search history.

(56) References Cited

U.S. PATENT DOCUMENTS

2006/0105360 A1* 5/2006 Croce et al. .................... 435/6

OTHER PUBLICATIONS

Costinean et al., "Pre-B cell proliferation and lymphoblastic leukemia/high-grade lymphoma in Eμ-miR155 transgenic mice", PNAS, vol. 103, No. 18, 7024-7029, May 2, 2006, The National Academy of Sciences of the USA.

Ambros, "The functions of animal microRNAs", Nature, vol. 431, 350-355, Sep. 16, 2004, Nature Publishing Group.
Hwang et al., "MicroRNAs in cell proliferation, cell death, and tumorigenesis", British Journal of Cancer, 94, 776-780, Feb. 21, 2006, Cancer Research UK.
Esquela-Kerscher et al., "Oncomirs—microRNAs with a role in cancer", Nature Reviews | Cancer, vol. 6, 259-269, Apr. 2006, Nature Publishing Group.
Lagos-Quintana et al., "Identification of Tissue-Specific MicroRNAs from Mouse", Current Biology, vol. 12, 735-739, Apr. 30, 2002, Elsevier Science Ltd.
Van Rooij et al., "A signature pattern of stress-responsive microRNAs that can evoke cardiac hypertrophy and heart failure", PNAS, vol. 103, No. 48, 18255-18260, Nov. 28, 2006, The National Academy of Sciences of the USA.
Ji et al., "MicroRNA Expression Signature and Antisense-Mediated Depletion Reveal an Essential Role of MicroRNA in Vascular Neointimal Lesion Formation", Circ. Res., 100, 1579-1588, 2007.

* cited by examiner

*Primary Examiner* — Kimberly Chong
(74) *Attorney, Agent, or Firm* — Pai Patent & Trademark Law Firm; Chao-Chang David Pai (57) ABSTRACT

The invention provides a method for determining if a subject has atherosclerosis, including: determining an endogenous microRNA-195 expression level of a subject suspected of having atherosclerosis; and comparing the endogenous microRNA-195 expression level of the subject with an endogenous microRNA-195 expression level of a normal group, wherein an increase in the endogenous microRNA-195 expression level of the subject as compared to the endogenous microRNA-195 expression level of the normal group indicates that the subject has atherosclerosis.

4 Claims, 6 Drawing Sheets

COMPOSITION AND METHOD FOR TREATING ATHEROSCLEROSIS, METHOD FOR DETERMINING IF A SUBJECT HAS ATHEROSCLEROSIS AND METHOD OF SCREENING AN ANTI-ATHEROSCLEROTIC DRUG

BACKGROUND OF THE INVENTION

1. Field of the Invention

The present invention relates to applications of microRNA-195, and in particular relates to applications of microRNA-195 with regard to atherosclerosis treatment and detection.

2. Description of the Related Art

MicroRNAs (miRNAs) are single-stranded RNA molecules of about 21-23 nucleotides in length, which regulate gene expression. mRNAs are first transcribed as a pri-miRNA with a cap and a poly-A tail and then processed to short, 70-nucleotide stem-loop structures known as pre-miRNA in a cell nucleus. The pre-miRNAs are then processed to mature miRNAs in the cytoplasm. A mature miRNA is complementary to a part of one or more messenger RNAs (mRNAs). Animal miRNAs are usually complementary to a site in the 3' untranslated region (UTR). Annealing of the miRNA to the mRNA inhibits protein translation, but sometimes facilitates cleavage of the mRNA.

MiRNAs are important regulators for cell growth, differentiation, and apoptosis (Costinean S, et al. Proc Natl Acad Sci USA. 2006; 103:7024-7029, Ambros V. 2004; 431:350-355 and Hwang H W, et al. Br J Cancer 2006; 94:776-780). Therefore, miRNAs may be important for normal development and physiology of cells. Consequently, dysregulation of miRNA may lead to human diseases. In this respect, an exciting research area is the role of miRNAs in cancer, given that cell dedifferentiation, growth, and apoptosis are important cellular events during the development of cancer. mRNAs are currently thought to function as both tumor suppressors and oncogenes (Esquelq-Kerscher A, et al. Nature Reviews Cancer. 2006; 6:259-269). Although miRNAs are expressed in the cardiovascular system (Lagos-Quintana M, et al. Curr Biol. 2002; 12:735-739), the role of miRNAs in atherosclerotic diseases are almost completely unknown. However, few studies have revealed the importance of miRNAs in cardiomyopathies (van Rooij E, et al. Proc Natl Acad Sci USA. 2006; 103:18255-18260). Nevertheless, the role of miRNAs in atherosclerotic diseases has yet to be fully investigated.

A tissue-specific expression is one important characteristic of miRNA expression. Specifically, one miRNA may be highly expressed in one tissue but have no or low expression in other tissues (Lagos-Quintana M, et al. Curr Biol. 2002; 12:735-739). A recent study using a rat model showed that 140 out of 180 tested miRNAs were expressed in the rat carotid arteries and 49 of the 140 were highly expressed in the rat normal arteries (Ji R, et al. Circ Res. 2007; 100:1579-1588).

BRIEF SUMMARY OF THE INVENTION

The invention provides a composition for treating atherosclerosis, comprising: an effective amount of microRNA-195 as an active ingredient for treating atherosclerosis; and a pharmaceutically acceptable carrier or salt.

The invention also provides a method for treating atherosclerosis in a subject in need thereof, comprising administering an effective amount of microRNA-195 to the subject in need thereof.

The invention further provides a method for determining if a subject has atherosclerosis, comprising: determining an endogenous microRNA-195 expression level of a subject suspected of having atherosclerosis; and comparing the endogenous microRNA-195 expression level of the subject with an endogenous microRNA-195 expression level of a normal group, wherein an increase in the endogenous microRNA-195 expression level of the subject as compared to the endogenous microRNA-195 expression level of the normal group indicates that the subject has atherosclerosis.

The invention further provides a method of screening an anti-atherosclerotic drug, comprising: treating a subject with an atherosclerosis inducing compound and a candidate drug; determining an endogenous microRNA-195 expression level of the subject; and comparing the endogenous microRNA-195 expression level of the subject with an endogenous microRNA-195 expression level of a control only treated with the atherosclerosis inducing compound, wherein a decrease in the endogenous microRNA-195 expression level of the subject as compared to the endogenous microRNA-195 expression level of the control indicates that the candidate drug has potential for treating atherosclerosis.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention is based on a discovery that microRNA-195 (miR-195) is related to atherosclerosis and is able to be used for treating atherosclerosis.

The "microRNA-195" in the invention refers to an original microRNA-195, a modified microRNA-195 (for example, a pre-microRNA-195 or all pyrimidine nucleotides in microRNA are replaced by their 2'-O-methyl analogs to improve microRAN stability) or a mimic of a microRNA-195 (for example, a synthetic microRNA-195 duplex). In one embodiment, the microRNA-195 may comprise an original human microRNA-195 (the sequence of which is SEQ ID NO: 1), a modified human microRNA-195, for example, a human pre-microRNA-195 (the sequence of which is SEQ ID NO:2 and consists of the sequence of original human microRNA-195, as set forth in SEQ ID NO:1, starting from the 15th nucleotide or a mimic of a human microRNA-195, for example, a synthetic microRNA-195 (such as Pre-miR™ miRNA, hsa-miR-195 (product ID PM10827), Ambion Inc.).

The invention uses a composition comprising a microRNA-195 as an active ingredient for treating atherosclerosis. The invention further provides a use for microRNA-195 for preparing a medicament for treating atherosclerosis. In one embodiment, the composition may comprise an effective amount of microRNA-195 and a pharmaceutically acceptable carrier or salt. In one embodiment, the microRNA-195 may be optionally packaged in the pharmaceutically acceptable carrier.

In another embodiment, a statin may be used in the composition of the invention. The statin may include, but is not limited to, simvastatin. Simvastatin is a lipid lowering drug belonging to the class of pharmaceuticals called "statins or HMGCoA reductase inhibitor." The composition of the invention may further comprise an effective amount statin. It is used to treat hypercholesterolemia (elevated cholesterol levels) and to prevent atherosclerotic diseases, such as myocardial infarction or stroke. The anti-atherosclerosis effect of the composition containing microRNA-195 along with statin is better than that of the composition containing only microRNA-195 and that of statin. The microRNA-195 and statin have a synergistic effect for treating atherosclerosis.

Panax Notoginseng is a widely used Chinese herb for the treatment of cardiovascular diseases, especially atherosclerosis. In another embodiment, a water extract of Panax Notoginseng or saponin which is the active ingredient of Panax Notoginseng may be used in the composition of the invention. The composition of the invention may further comprise an effective amount of water extract of Panax Notoginseng or saponin. The anti-atherosclerosis effect of the composition containing microRNA-195 along with the water extract of Panax Notoginseng or saponin is better than that of the composition containing only microRNA-195.

A method for treating atherosclerosis may be also included in the invention. The method for treating atherosclerosis may comprise administering an effective amount of a microRNA-195 to a subject in need thereof. The subject may comprise a mammal and in one embodiment, the mammal may comprise a human. In one embodiment, the microRNA-195 may be optionally packaged in a pharmaceutically acceptable carrier.

In another embodiment, the method for treating atherosclerosis may further comprise administering an effective amount of statin to a subject. The statin may include, but is not limited to, simvastatin. It is noted that the microRNA-195 and the statin may be administered at the same time or microRNA-195 may be administered first or statin may be administered first. The anti-atherosclerosis effect for administering microRNA-195 along with statin is better than that of administering only microRNA-195 and that of administering only statin. The microRNA-195 and statin have a synergistic effect for treating atherosclerosis. Furthermore, microRNA-195 may enhance statin effect for treating atherosclerosis and reduce the statin dose or reduce the statin-induced side effects for treating atherosclerosis.

In another embodiment, the method for treating atherosclerosis may further comprise administering an effective amount of water extract of Panax Notoginseng or saponin which is the active ingredient of Panax Notoginseng to a subject. It is noted that the microRNA-195 and the water extract of Panax Notoginseng or saponin may be administered at the same time or microRNA-195 may be administered first or the water extract of Panax Notoginseng or saponin may be administered first. The anti-atherosclerosis effect for administering microRNA-195 along with the water extract of Panax Notoginseng or saponin is better than that of administering only microRNA-195.

A pharmaceutically acceptable carrier may comprise, but is not limited to, a solvent, a dispersion medium, a liposome, a lipidic particle, a coating, a viral vector, a plasmid vector, or an isotonic and absorption delaying agent. The viral vector may include, but is not limited to, an adenovirus, an adeno-associated virus, a vaccinia virus, a retrovirus (lentivirus), etc. The pharmaceutical composition can be formulated into dosage forms for different administration routes utilizing conventional methods.

The pharmaceutically acceptable salt may comprise, but is not limited to, inorganic cation salts including alkali metal salts such as sodium salt, potassium salt or amine salt, alkaline-earth metal salt such as magnesium salt or calcium salt, the salt containing bivalent or quadrivalent cation such as zinc salt, aluminum salt or zirconium salt. In addition, the pharmaceutically acceptable salt may also comprise organic salt including dicyclohexylamine salt, methyl-D-glucamine, and amino acid salt such as arginine, lysine, histidine, or glutamine.

The composition of the invention may be administered orally, para-enterally or by an inhalation spray or via an implanted reservoir. Also the administration route in the method for treating atherosclerosis may comprise oral administration or para-enteral administration.

An oral composition can comprise, but is not limited to, tablets, capsules, emulsions and aqueous suspensions, dispersions and solutions.

Orally administered preparations may be in the form of solids, liquids, emulsions, suspensions, or gels, or preferably in a unit dosage form, for example as tablets or capsules. Tablets may be compounded in combination with other ingredients customarily used, such as talc, vegetable oils, polyols, gums, gelatin, starch, and other carriers. The lipid vesicles may be dispersed in or combined with a suitable liquid carrier in solutions, suspensions, or emulsions.

Para-enteral compositions intended for injection, either subcutaneously, intramuscularly, or intravenously, can be prepared with liquids or solid forms for a solution in liquid prior to injection, or as emulsions. Such preparations are sterile, and liquids to be injected intravenously should be isotonic. Suitable excipients are, for example, water, dextrose, saline, and glycerol.

Para-enteral administration is generally characterized by injection. The para-enteral method may comprise subcutaneous, intracutaneous, intravenous, intramuscular, intraarticular, intraarterial, intrasynovial, intrasternal, intrathecal, and intraleaional, as well as infusion techniques. A more recently revised approach for para-enteral administration involves use of a slow release or sustained release system, such that a constant level of dosage is maintained.

In the present invention, it was discovered that the endogenous microRNA-195 expression level of subjects with atherosclerosis were higher than that of healthy subjects, and that may due to a nature defense mechanism. The endogenous microRNA-195 may be used as a biomarker for atherosclerosis. A method for determining if a subject has atherosclerosis is provided in the invention. The method for determining if a subject has atherosclerosis may comprise the steps as described in the following.

First, an endogenous microRNA-195 expression level of a subject suspected of having atherosclerosis may be determined. The subject may comprise a mammal and the mammal may comprise human. In one embodiment, the endogenous microRNA-195 expression level of the subject may be determined by analyzing a sample of the subject. The sample may comprise plasma, serum or a tissue, etc. In one embodiment, the tissue may comprise blood vessel walls.

Next, the endogenous microRNA-195 expression level of the subject and an endogenous microRNA-195 expression level of a normal group are compared. An increase in the endogenous microRNA-195 expression level of the subject as compared to the endogenous microRNA-195 expression level of the normal group may indicate that the subject may have atherosclerosis. In one embodiment, the endogenous microRNA-195 expression level of the normal group may be a mean of an endogenous microRNA-195 expression level of the respective normal group subjects.

In addition, in the present invention, it was further discovered that when an atherosclerosis inducing compound treated cell is treated with the anti-atherosclerosis medicine known in the art, such as statin or Panax Notoginseng, the endogenous microRNA-195 expression level of the cell was lower when compared with that of an atherosclerosis inducing compound treated cell which was not treated with the anti-atherosclerosis medicine. Therefore, the endogenous microRNA-195 may be used as a drug target for screening an anti-atherosclerotic drug. A method of screening an anti-atherosclerotic drug is provided in the invention. The method of screening an anti-atherosclerotic drug may comprise the steps as described in the following.

First, a subject is treated with an atherosclerosis inducing compound and a candidate drug. The atherosclerosis inducing compound and the candidate drug may be treated to the subject at the same time. The subject may comprise a cell or mammal. The cell may comprise a vascular smooth muscle cell. The atherosclerosis inducing compound may comprise ox-LDL.

Next, an endogenous microRNA-195 expression level of the subject may be determined. When the subject is a mammal, the endogenous microRNA-195 expression level of the subject may be determined by analyzing a sample of the subject and the sample may comprise plasma, serum or a tissue, etc. In one embodiment, the tissue may comprise blood vessel walls.

Then, the endogenous microRNA-195 expression level of the subject and an endogenous microRNA-195 expression level of a control only treated with the atherosclerosis inducing compound are compared. A decrease in the endogenous microRNA-195 expression level of the subject as compared to the endogenous microRNA-195 expression level of the control may indicate that the candidate drug has potential for treating atherosclerosis.

In the present invention, first, microRNA-195 can be used to treat or prevent atherosclerosis. Second, a combined therapy method comprising statin or Panax Notoginseng with microRNA-195 may be used to increase therapeutic effect of atherosclerosis. Third, microRNA-195 may be used as a biomarker for determining atherosclerosis. Fourth, microRNA-195 can be used as a biomarker to screen compounds/drugs to find potential anti-atherosclerosis drugs.

EXAMPLE

Part 1

Cell Culture

The experiments were conducted in the primary aortic smooth muscle cells (purchased as cryopreserved tertiary cultures from Cascade Biologics, OR, USA) at passages 4 to 8. The VSMC cells were maintained in an M231 culture medium supplemented with fetal bovine serum (FBS, 5%), human epidermal growth factor (10 ng/ml), human basic fibroblast growth factor (3 ng/ml), insulin (10 mg/ml), penicillin (100 units/ml), streptomycin (100 pg/ml), and Fungizone (1.25 mg/ml). The cultures were kept at a temperature of 37° C. in an atmosphere of 5% $CO_2$ in air.

Part 2

Global MicroRNA Detection

Control cells were treated with ox-LDL (concentration of 40 μg/ml) that was used as a stimulant for atherosclerosis, and experimental cells were treated with ox-LDL (concentration of 40 μg/ml) and the Chinese herbal medicine Panax Notoginseng (in a form of water extract with concentration of 1 mg/ml; Chuang Song Zong Pharmaceutical co. Ltd). After a 4 hour treatment, cytoplasmic RNA was extracted from the cultured cells using a Trizol reagent (Invitrogen) according to the manufacturer protocol. The concentration and integrity of total RNA were determined using the NanoPhotometer™ spectrophotometer (IMPLEN GmbH, Munich, Germany). The global microRNA expression profile was measured using the TaqMan Array Human MicroRNA Array Set V.2.0® (Applied Biosystems Inc. ABI). The endogenous abundance of microRNAs was analyzed in an ABI PRIZM 7900 sequence detection system. Differentially expressed miRNAs were calculated by StatMiner software. The results are shown in Table 1.

TABLE 1

MicroRNA expression profile of VSMC after a Chinese herbal medicine (Panax Notoginseng) treatment

|  | Up regulation | Fold change |  | Down regulation | Fold change |
|---|---|---|---|---|---|
| Top 10 | miR-204 | 2.18 | Top 10 | miR-195 | 5.12 |
|  | miR-106b | 1.81 |  | miR-379 | 4.34 |
|  | miR-223 | 1.76 |  | miR-20a | 2.35 |
|  | miR-485 | 1.64 |  | miR-15b | 2.34 |
|  | miR-433 | 1.46 |  | miR-137 | 2.29 |
|  | miR-425 | 1.41 |  | Let-7b | 2.21 |
|  | miR-532 | 1.39 |  | miR-92a | 2.17 |
|  | miR-495 | 1.23 |  | miR-431 | 1.99 |
|  | miR-191 | 1.14 |  | miR-221 | 1.96 |
|  | miR-214 | 1.10 |  | miR-30b | 1.94 |

As shown in Table 1, among the 667 microRNAs in the array, 7 microRNAs showed decreased expression by at least 2-fold in the cells treated with the Chinese herbal medicine Panax Notoginseng. Three of the seven microRNAs with decreased expressions were in the miR-15 family, and microRNA-195 showed the most significant decrease. Accordingly, microRNA-195 was identified as a potential anti-atherosclerotic biomarker.

Part 3

Confirming a Novel Anti-Atherosclerotic Effect of miRNA-195

According to the global microRNA expression data, it was shown that microRNA-195 had the most significant change between treated and untreated cells with Panax Notoginseng. Then, microRNA-195 (Pre-miR™ miRNA, hsa-miR-195 (product ID PM10827), Ambion Inc., which mimics precursor for mature human miR-195) was transfected into the VSMC cells simultaneously treated with ox-LDL to confirm the miRNA-195 anti-atherosclerosis effect.

The transfection was performed using a siPort NeoFx reagent (Ambion) and VSMC cell proliferation and migration were evaluated 24 hours after the microRNA-195 transfection. In addition, simvastatin was used, a widely used lipid lowering drug and anti-atherosclerosis drug, to test the influence of microRNA-195 levels by simvastatin.

Cell Proliferation Assay

VSMC is an established model for atherosclerosis studies and when atherosclerosis incursion VSMC proliferation increases. A VSMC proliferation rate was used as a surrogate for the development of atherosclerosis, which was assessed by WST-1. By using a 1-3 μL siPort NeoFx (Ambion) reagent, 0-120 nM of microRNA-195 (Pre-miR™ miRNA, hsa-miR-195 (product ID PM10827), Ambion Inc.) was transfected into the VSMC cells while they were incubated with ox-LDL (40 μg/ml) for 24 hours. To measure cell proliferation, the microplates were incubated at a temperature of 37° C. with 5% $CO_2$ in air for 24 hours, after which 10 μL of WST-1 (Roche Applied Science, Indianapolis, Ind.) was added into each well and incubated for 30 minutes at a temperature of 37° C. The microplates were then read by a spectrophotometer by measuring the absorbance of a dye with a wavelength of 450 nm and a reference wavelength of 600 nm (Benchmark PLUS Microplate Spectrophotometer, Bio-Rad) and plotted. Each experiment had three replications. The results are shown in FIG. 1.

Figure 1:
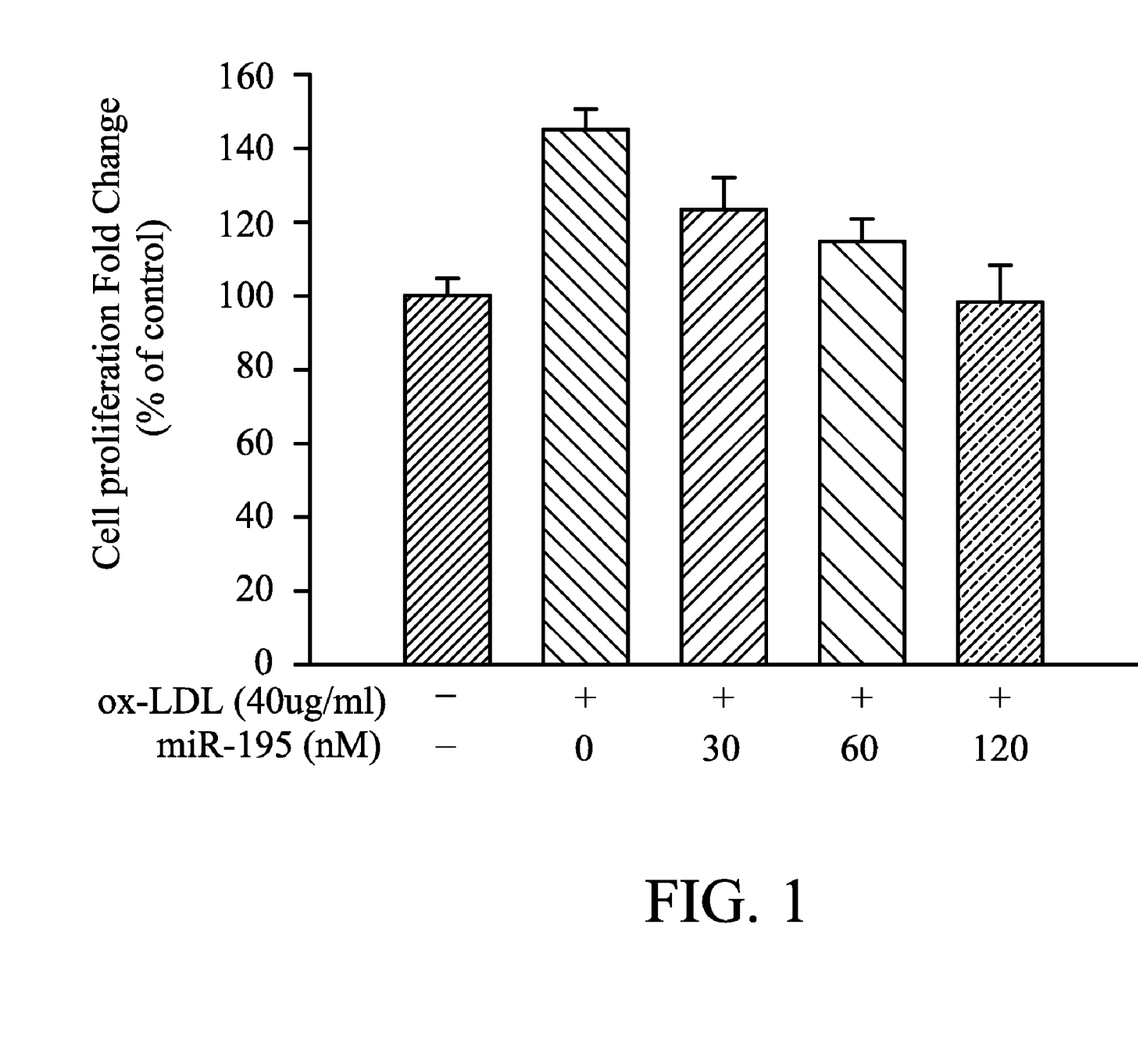
FIG. 1 shows the WST-1 assay results for cell proliferation of the vascular smooth muscle cells (VSMC) treated with different concentrations of microRNA-195 (miR-195)

As shown in FIG. 1, ox-LDL (40 μg/ml) caused a significant increase in the cell proliferation by 144.8% over the basal level using the WST-1 assay. Transfecting microRNA-195 with concentrations of 30, 60 and 120 nM resulted in a concentration-dependent reduction of VSMC cell proliferation by 21%, 29% and 45%, respectively. It is shown that microRNA-195 exerts a dose-dependent effect on anti-proliferation.

Figure 2:
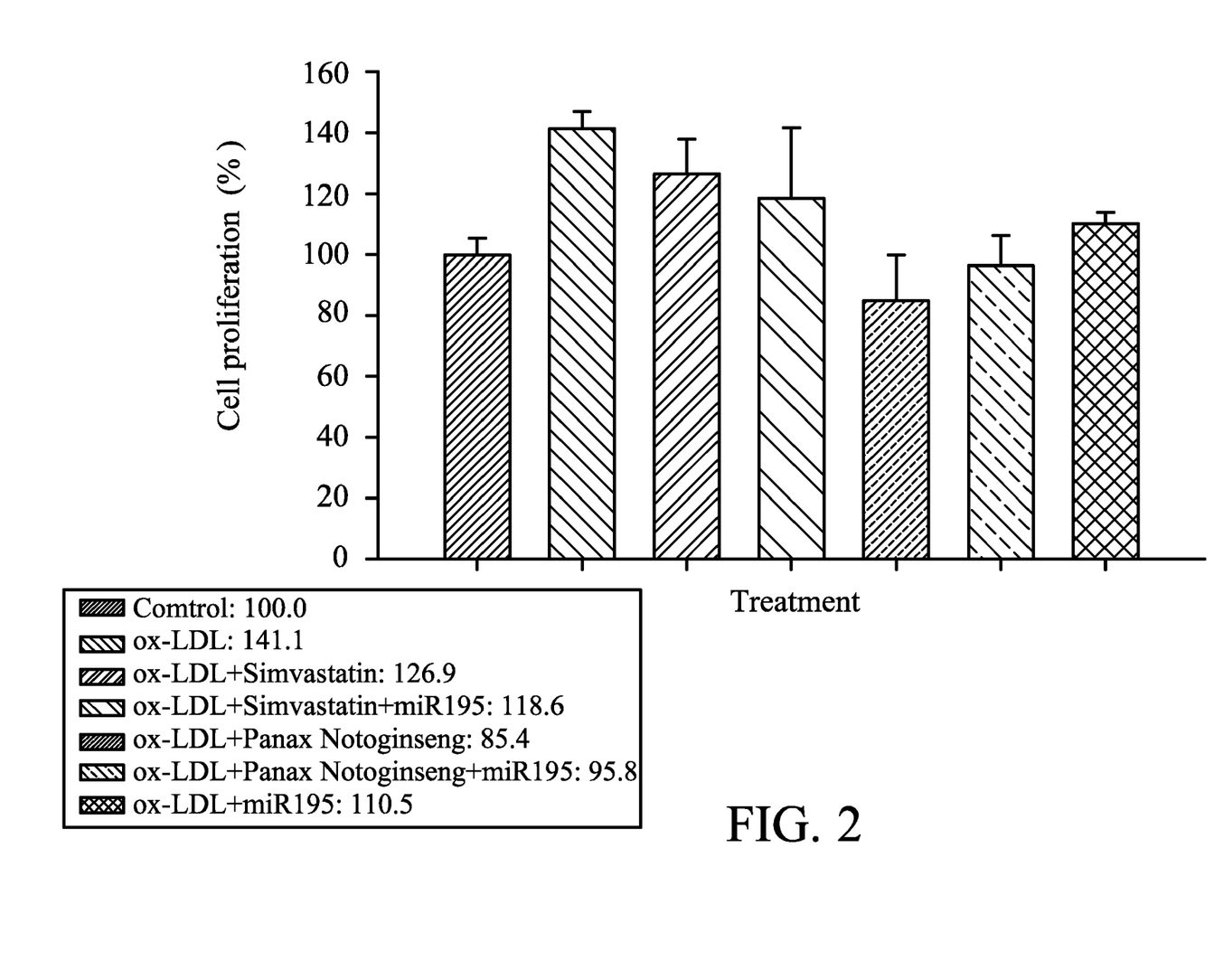
FIG. 2 shows the WST-1 assay results for cell proliferation of the VSMC cells with different treatments.

Cell proliferation of the VSMC was evaluated following incubation in ox-LDL (40 μg/ml) for 24 hours in the presence of microRNA-195 (Pre-miR™ miRNA, hsa-miR-195 (product ID PM10827), Ambion Inc.) (100 nM), simvastatin (1 nM) or Panax Notoginseng (in a form of water extract with concentration of 1 mg/ml; Chuang Song Zong Pharmaceutical co. Ltd), or in the presence of microRNA-195 (100 nM) with simvastatin (1 nM) or with Panax Notoginseng (in a form of water extract with concentration of 1 mg/ml). The WST-1 assay was also used to compare the cell proliferation level (anti-atherosclerotic effect) among the different treatments. The results are shown in FIG. 2. As shown in FIG. 2, the results indicated that the inhibition of the VSMC proliferation was stronger when the cells were treated with microRNA-195 plus simvastatin (1 nM) compared with microRNA-195 or simvastin alone. Our results suggest that microRNA-195 and simvastatin had a synergistic effect for treating atherosclerosis. Accordingly, microRNA-195 may enhance simvastatin effect for treating atherosclerosis and reduce the simvastatin dose or reduce the simvastatin-induced side effects for treating atherosclerosis.

Chemotactic Migration

Chemotactic migration is another characteristic of atherosclerosis and can be used as another line of evidence of atherosclerotic change for the cultured VSMC cells. This experiment was assayed by using a microchemotactic chamber and polycarbonate filters with pores of 8 mm in diameter (Transwell, Millipore). After incubated with microRNA-195 (Pre-miR™ miRNA, hsa-miR-195 (product ID PM10827), Ambion Inc.) (100 nM) or an inhibitor (100 nM) for 24 hours, the VSMC cells were trypsinized and suspended with a serum free medium. A volume (300 μl) of a $1 \times 10^4$ cell suspension was placed in the upper chamber, the medium containing ox-LDL (40 μg/ml, each) was placed in the lower and upper chamber. The cell suspension was incubated at a temperature of 37° C. under 5% $CO_2$ in air for 24 hours. After incubation, the VSMC cells on the upper side of the filter were scraped off, and the cells that had directly migrated to the lower side of the filter were trypsinized. The cells were fixed with methanol and stained with a Giemsa solution (Merck). Quantification of chemotactic migration was performed using the hemocytometer. The results were expressed as percentages of migrated cells as compared to the control medium cells and shown in FIG. 3.

Figure 3:
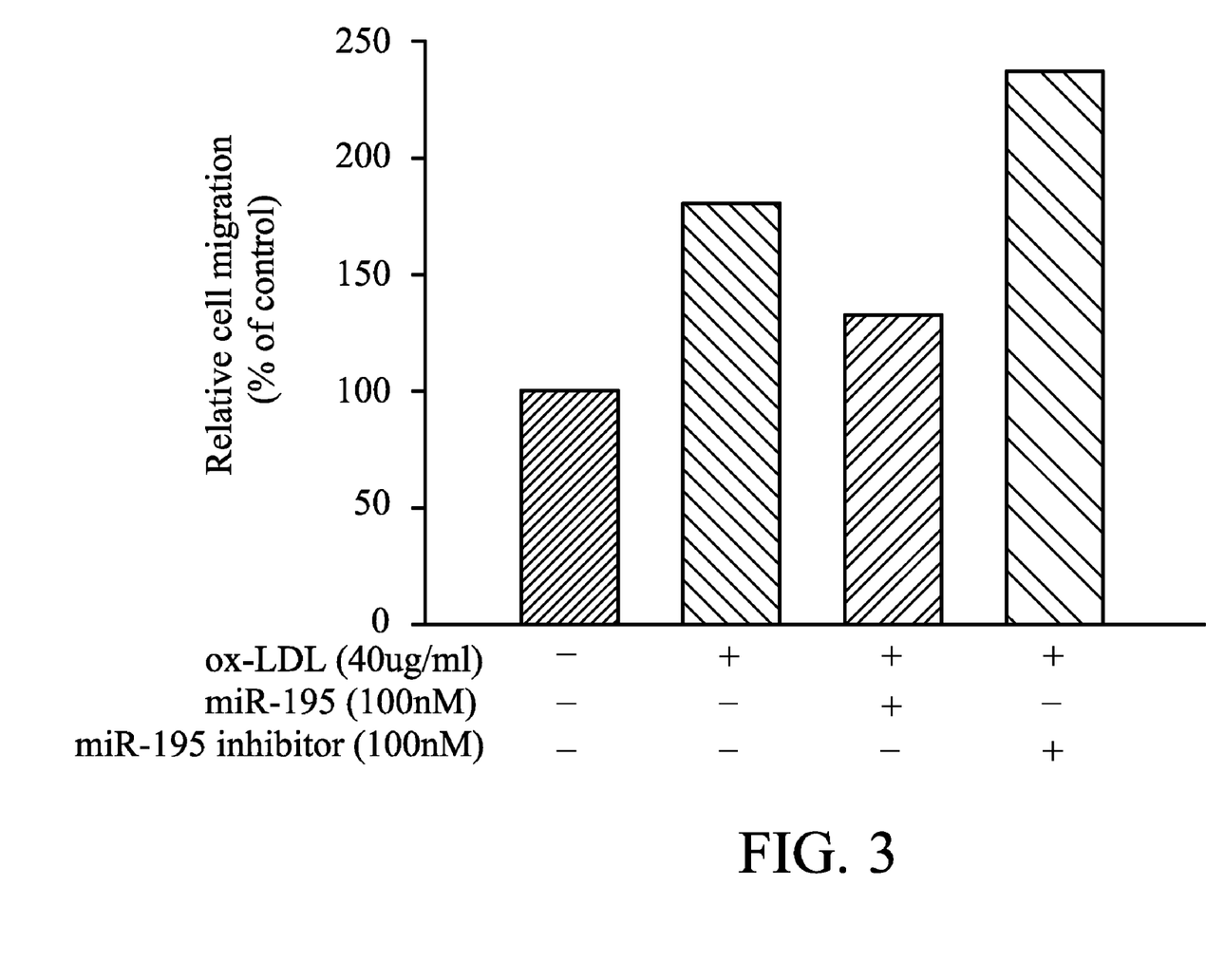
FIG. 3 shows the cell migration level of the VSMC cells treated with microRNA-195 and microRNA-195 inhibitor.

As shown in FIG. 3, ox-LDL (40 μg/ml) significantly stimulated chemotactic migration by 180.1% over the basal level. In the presence of microRNA-195 (Pre-miR™ miRNA, hsa-miR-195 (product ID PM10827), Ambion Inc.) (100 nM), the migration was significantly suppressed to 137.6%. Meanwhile, using the microRNA-195 inhibitor (100 nM) significantly increased migration to 233.7% in comparison to the control. Since VSMC migration is also a cellular phenotype to indicate atherosclerosis, the results shown in FIG. 3 clearly demonstrate that microRNA-195 has an anti-atherosclerosis effect.

The Influence of miRNA-195 on an Atherosclerotic Biomarker

Monocyte chemotactic protein-1 (MCP-1) is a well established atherosclerotic biomarker and it was examined to further test for the influence of microRNA-195 on the atherogenic biomarker. VSMC cells in six-well plates were grown to confluence and then cultivated in a serum-free medium for 24 hours before the experiment. After transfection of microRNA-195 for 24 hours, the cells were further incubated with ox-LDL and simvastatin for another 24 hours. The supernatants of the conditioned medium were collected and frozen at −70° C. The culture supernatants were analyzed to determine the MCP-1 using Sandwich Enzyme Immunoassay kits (BD Biosciences) according to the manufacturer protocol. The results are shown in FIG. 4.

Figure 4:
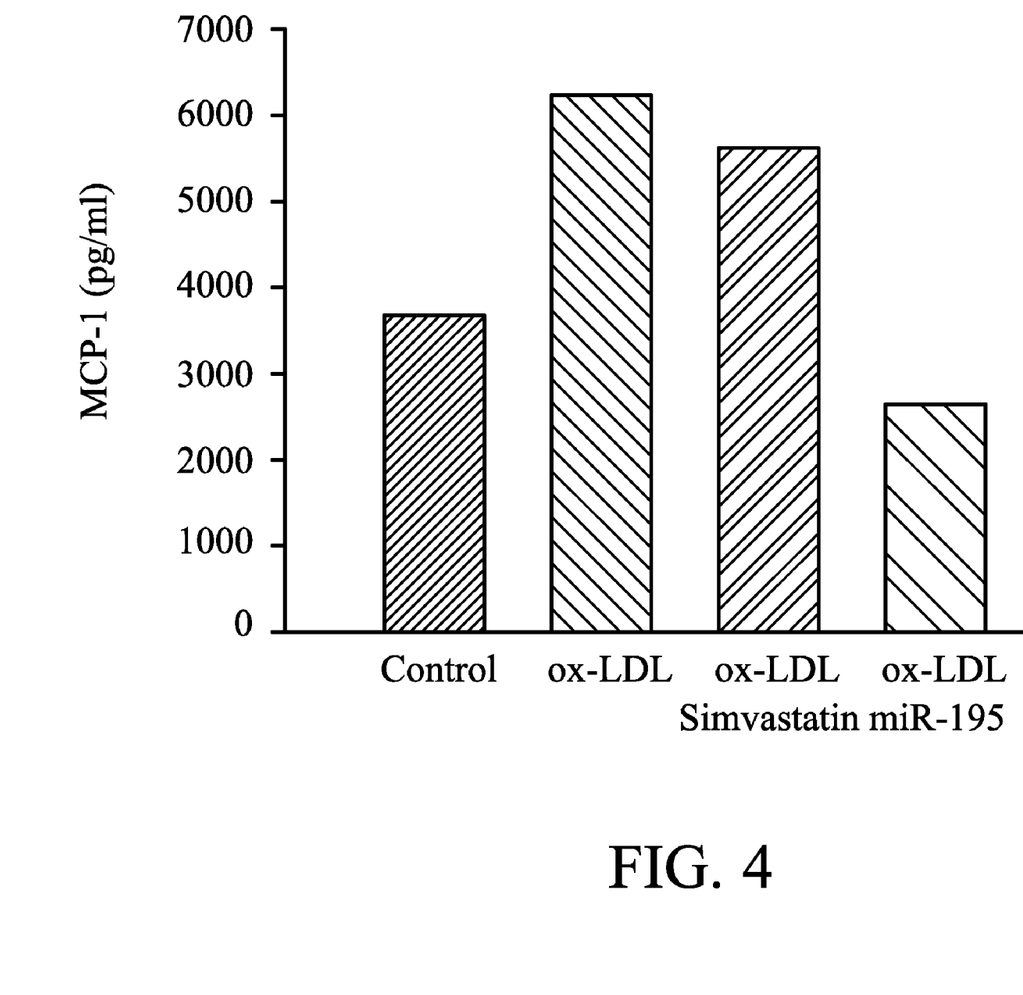
FIG. 4 shows the expression levels of an atherosclerotic biomarker, MCP-1, secreted from the VSMC cells treated with simvastatin or microRNA-195 in the presence of ox-LDL stimulation.

As shown in FIG. 4, microRNA-195 can significantly decrease MCP-1 levels. MicroRNA-195 has a stronger effect on reducing the atherogenic biomarker than simvastatin.

According to all of results in the Part 3, microRNA-195 has a strong anti-atherosclerosis effect and ability for treating atherosclerosis.

Part 4

The Serum Level of miRNA-195 in Human Subjects

The serum levels of microRNA-195 from the general population and patients who received coronary angiography were measured. Approximately 6 ml venous blood was collected from an antecubital fossa and placed in a serum separator tube. The blood was centrifuged at 1600 rpm for 5 min and then serum obtained therefrom was aliquoted into 1.7 ml Eppendorf tubes, followed by 15 minutes of high speed centrifugation at 12,000 rpm to completely remove cell debris, leaving only circulating RNA. Total RNA which included miRNA in 400 μl of serum was isolated by using a MasterPure™ complete RNA purification kit according to the manufacturer protocol (Epicentre). The RNA was stored at a temperature of −80° C. until use. The endogenous abundance of microRNAs was determined in an ABI PRISM 7500 sequence detection system using the quantitative real-time PCR method. Each sample was performed in triplicates. The typical amplification program was carried out in a 20 μl reaction with a primer at a final concentration of 300 nM and probes of 200 nM. Serial dilutions of control cDNA for generating standard curves ran in duplicate. Real-time PCR results were analyzed using the ABI PRISM 7500 SDS software. Relative differences of microRNAs were quantified using the ΔΔCt method. For graphical presentation, the $2^{-\Delta\Delta Ct}$ transformation was used according to the ABI user bulletin version #2. Expression values were depicted relatively to the value at baseline which was the earliest time point present in all the experiments. The results are shown in FIG. 5.

Figure 5:
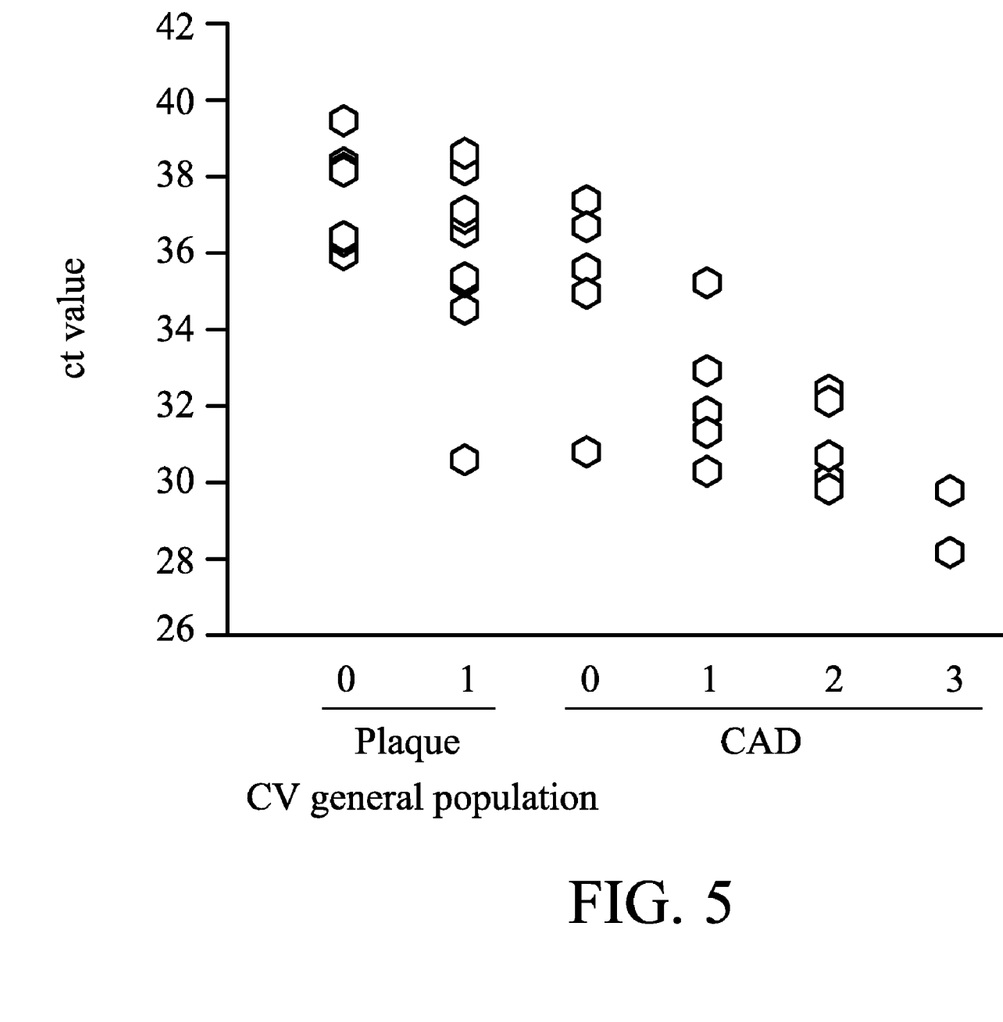
FIG. 5 shows the expression levels of microRNA-195 in the general population (the subjects were further divided into plaque=0 or 1) and the patients with coronary artery stenosis (the subjects were further divided into CAD=0, 1, 2, and 3), respectively.

As shown in FIG. 5, microRNA-195 has a great potential for the clinical application because it can be detected from peripheral blood. When microRNA-195 serum levels (i.e. endogenous microRNA-195) among the general population were compared with those from the patients who received coronary angiography, it was found that the serum microRNA-195 levels have a clear pattern with the severity of atherosclerosis. Notably, the higher Ct value shown in FIG. 5, the lower microRNA-195 concentration. We separated the general population according to their severity of atherosclerosis measured in the carotid artery: plaque=0 means no evidence of atherosclerosis and plaque=1 means detectable carotid atherosclerosis but without clinical symptoms. The patients receiving coronary angiography can be divided into 4 severity categories: CAD=0 means the stenosis of coronary artery is less than 50% in any of the three major coronary arteries, CAD=1 means the stenosis is greater than 50% in one of the three major coronary arteries, CAD=2 means the stenosis is greater than 50% in two of the three major coronary arteries and CAD=3 means the stenosis is greater than 50% in all three major coronary arteries). Clearly, the subjects with more severe atherosclerosis had higher microRNA-195 levels. To summarize: the endogenous microRNA-195 expression level of subjects with atherosclerosis is higher than that of healthy subjects which may result from a nature defense mechanism. That is, microRNA-195 is an endogenous protective factor for atherosclerosis and thus microRNA-195 will increase when a subject develops atherosclerosis. Moreover, according to the results in the Part 4, microRNA-195 may be used as an atherosclerotic biomarker for determining if a subject has atherosclerosis.

Part 5

The miRNA-195 Expression Level in the Blood Vessel of Human Subjects

Tissue Samples from
Paraformaldehyde-fixed paraffin-embedded (FFPE) arterial blood vessel samples from human subjects with or without atherosclerosis were acquired. The paraffin blocks were cut into 10-1 μm sections. Total RNA from the FFPE tissues block was isolated using the commercially available kits, RecoverAll Total Nucleic Acid Isolation Kit (Ambion), according to the manufacturers' instructions. Paraffin-embedded samples are incubated in xylene at elevated temperatures to solubilize and remove paraffin from the tissue, then washed in alcohol solutions to remove the xylene. After deparaffinization, it was mixed with 400 μl of digestion buffer and 4 μl of protease and was incubated at 50° C. for three hours for RNA isolation. The prepared specimen was added to 480 μl isolation additive and vortex, and then passed through a filter cartridge and incubated for five minutes. Washing was performed three times and the results were centrifuged to remove residual fluid. DNase mix was added to each filter cartridge and they were incubate for 30 minutes before elution with nucleic acid with 20 μl DEPC-distilled water and incubation for five minutes and storage at −80° C. Concentration and purity of the total RNA samples were measured using the NanoPhotometer™ spectrophotometer (IMPLEN GmbH, Munich, Germany).

Reverse Transcription and Quantitative Real-Time PCR

The RNA was stored at −80° C. until use. The endogenous abundance of microRNAs was performed in an ABI PRIZM 7500 sequence detection system. Quantitative real-time PCR was performed in triplicates. The typical amplification program is carried out in a 20 μl reaction with primer at a final concentration of 300 nM and probes of 200 nM. Serial dilutions of control cDNA for generating standard curves will run in duplicate. Real-time PCR results can be analyzed using the ABI PRISM 7500 SDS software. Relative differences of microRNAs were quantified using the ΔΔCt method. For graphical presentation, we will use the $2^{-\Delta\Delta Ct}$ transformation according to the ABI user bulletin version #2. Expression values depict relatively to the value at baseline which is the earliest time point present in all the experiments.

The result showed that Ct value was 35.6 for the normal tissue and 34.9 for the atherosclerotic tissue. A lower Ct value which means a higher microRNA-195 in the atherosclerotic blood vessels is comparable with what observed in the serum samples as shown in FIG. 5.

Part 6

Confirmation of Endogenous microRNA of Cells with Different Treatments

The endogenous abundance of microRNAs that showed differential expressions between experimental (simvastatin, Panax Notoginseng, ox-LDL plus simvastatin or Panax Notoginseng) and control (ox-LDL) cells were measured. Quantitative real-time PCR was performed in an ABI PRIZM 7500 sequence detection system in triplicates. The typical amplification program was carried out in a 20 μl reaction with a primer at a final concentration of 300 nM and probes of 200 nM. Serial dilutions of control cDNA for generating standard curves ran in duplicate. Real-time PCR results were analyzed using ABI PRISM 7500 SDS software. Relative differences of microRNAs were quantified using the ΔΔCt method. For graphical presentation, the $2^{-\Delta\Delta Ct}$ transformation was used according to the ABI user bulletin version #2. Expression values were depicted relatively to the value at baseline which was the earliest time point present in all the experiments. The results are shown in FIG. 6.

Figure 6:
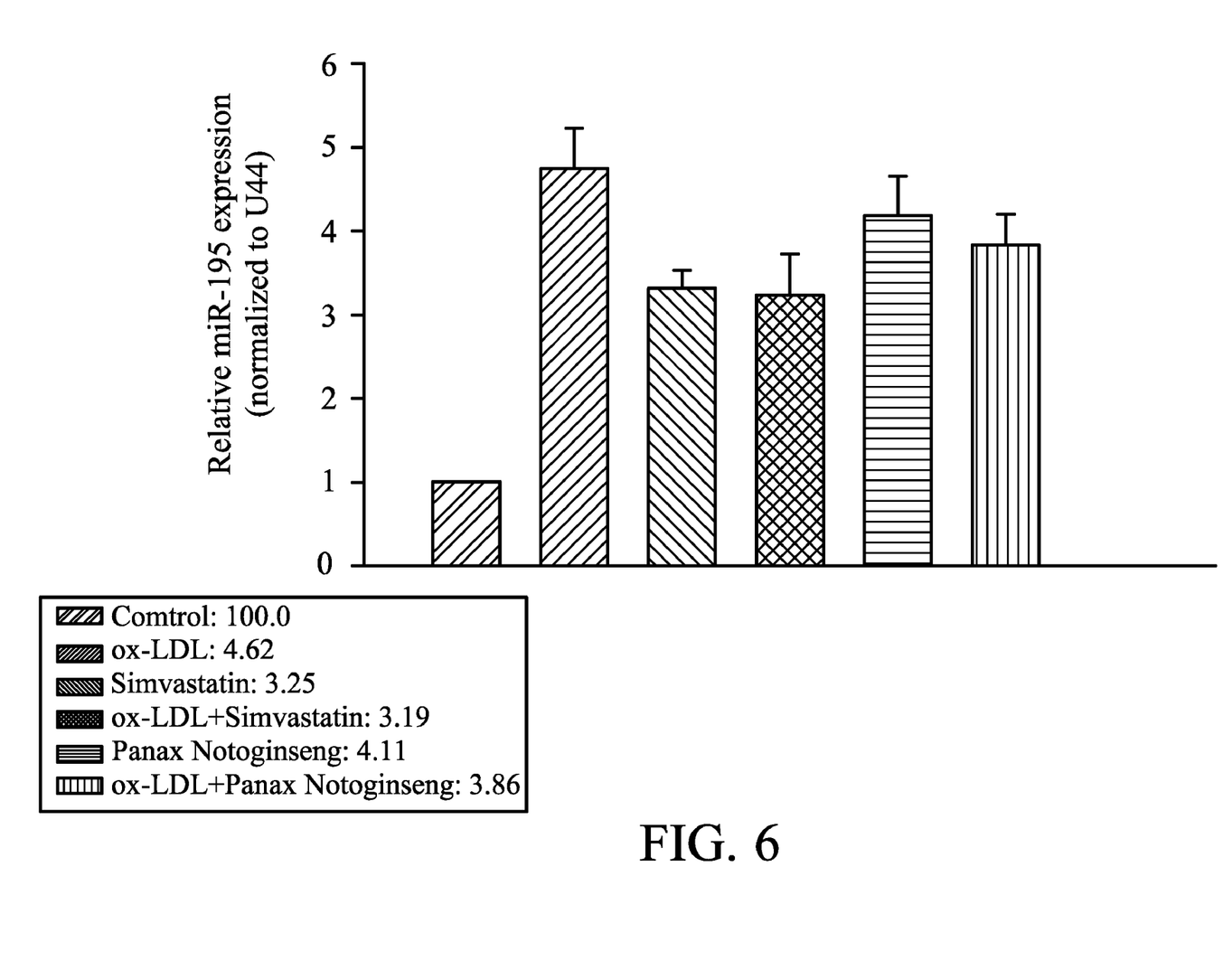
FIG. 6 shows the expression levels of microRNA-195 of the VSMC cells treated with simvastatin or Panax Notoginseng in the presence and absence of ox-LDL stimulation. The microRNA-195 abundance was normalized to U44.

As shown in FIG. 6, in order to verify the accuracy of the microarray results in the ox-LDL-stimulated VSMC, the change of endogenous microRNA-195 in the VSMC was measured after being normalized to U44. The results indicated that microRNA-195 expression of the untreated cells was increased by 4.3-fold after treatment with ox-LDL for 24 hours. After the treatment with ox-LDL and simvastatin (1 nM) or Panax Notoginseng (1 mg/ml) for 24 hours, the endogenous microRNA-195 decreased by more than a 0.68-fold and 0.84-fold than in the ox-LDL-stimulated cells. Moreover, according to the results in the Part 5, microRNA-195 can be a potential drug target for screening an antiatherosclerotic drug since the expression of microRNA-195 decreased by simvastatin and Panax Notoginseng which are known medicine for treating atherosclerosis.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A composition for treating atherosclerosis, comprising:
an effective amount of microRNA-195 as an active ingredient for treating atherosclerosis;
an effective amount of statin; and
a pharmaceutically acceptable carrier or salt.

2. The composition for treating atherosclerosis as claimed in claim 1, wherein the statin comprises simvastatin.

3. A composition for treating atherosclerosis, comprising:
an effective amount of microRNA-195 as an active ingredient for treating atherosclerosis;
an effective amount of water extract of Panax Notoginseng; and
a pharmaceutically acceptable carrier or salt.

4. A composition for treating atherosclerosis, comprising:
an effective amount of microRNA-195 as an active ingredient for treating atherosclerosis;
an effective amount of saponin; and
a pharmaceutically acceptable carrier or salt.

* * * * *

SEQUENCE LISTING

<160> NUMBER OF SEQ ID NOS: 2

<210> SEQ ID NO 1
<211> LENGTH: 21
<212> TYPE: RNA
<213> ORGANISM: Homo sapiens

<400> SEQUENCE: 1
uagcagcaca gaaauauugg c                                               21

<210> SEQ ID NO 2
<211> LENGTH: 87
<212> TYPE: RNA
<213> ORGANISM: Homo sapiens

<400> SEQUENCE: 2
agcuucccug gcucuagcag cacagaaaua uuggcacagg gaagcgaguc ugccaauauu     60
ggcugugcug cuccaggcag gguggug                                         87